US012617748B2

(12) United States Patent
Bhaumik et al.

(10) Patent No.: US 12,617,748 B2
(45) Date of Patent: May 5, 2026

(54) PROCESS FOR RECYCLING OF POLYETHYLENE TEREPHTHALATE (PET) WASTE

(71) Applicant: FILATEX INDIA LIMITED, Gujarat (IN)

(72) Inventors: Kasinath Bhaumik, Gujarat (IN); Anupam Acharya, Gujarat (IN); Madhu Sudhan Bhageria, New Delhi (IN); Ashok Chauhan, New Delhi (IN); Vyanu Vyas, Gujarat (IN)

(73) Assignee: FILATEX INDIA LIMITED, Gujarat (IN)

( * ) Notice: Subject to any disclaimer, the term of this patent is extended or adjusted under 35 U.S.C. 154(b) by 410 days.

(21) Appl. No.: 18/036,881

(22) PCT Filed: Jan. 21, 2022

(86) PCT No.: PCT/IB2022/050519
§ 371 (c)(1),
(2) Date: May 13, 2023

(87) PCT Pub. No.: WO2022/254258
PCT Pub. Date: Dec. 8, 2022

(65) Prior Publication Data
US 2023/0416183 A1      Dec. 28, 2023

(30) Foreign Application Priority Data

Jun. 2, 2021    (IN) .............................. 202121024616

(51) Int. Cl.
| C07C 67/03 | (2006.01) |
| B01J 19/00 | (2006.01) |
| B01J 19/24 | (2006.01) |
| C08J 11/24 | (2006.01) |

(52) U.S. Cl.
CPC ........... C07C 67/03 (2013.01); B01J 19/0013 (2013.01); B01J 19/245 (2013.01); C08J 11/24 (2013.01); C08J 2367/02 (2013.01)

(58) Field of Classification Search
CPC ... B01J 19/0013; B01J 19/245; C08G 63/183; C08G 63/916
See application file for complete search history.

(56) References Cited

U.S. PATENT DOCUMENTS

| 7,211,193 B2 | 5/2007 | Inada et al. |
| 7,462,649 B2 | 12/2008 | Nakao et al. |

| 2004/0182782 A1 | 9/2004 | Inada et al. | |
| 2021/0024718 A1 | 1/2021 | Fang et al. | |
| 2022/0118763 A1 | 4/2022 | Korthuis et al. | |
| 2022/0325064 A1* | 10/2022 | Atkins ..................... | C08J 11/24 |

FOREIGN PATENT DOCUMENTS

| CN | 107266664 A | 10/2017 |
| EP | 0723951 A1 | 7/1996 |
| EP | 3778744 A1 | 2/2021 |
| JP | 2003055300 A | 2/2003 |
| JP | 5189266 B2 | 4/2013 |
| WO | 2021002869 A1 | 1/2021 |

OTHER PUBLICATIONS

WO2022254258 PCT/IB2 022/050519 International Search Report, Apr. 7, 2022.
WO2022254258 PCT/IB2 022/050519 Written Opinion, Apr. 7, 2022.
Hu, Yuanchao, Yong Wang, Xuzhen Zhang, Jun Qian, Xiquan Xing, and Xiuhua Wang. "Synthesis of poly (ethylene terephthalate) based on glycolysis of waste PET fiber." Journal of Macromolecular Science, Part A 57, No. 6 (2020): 430-438.
Kim et al. journal articles , "Effect of Polycondensation Catalyst on Fiber Structure Development in High-Speed Melt Spinning of Poly (Ethylene Terephthalate )", Polymers 2019, 11, 1931; doi:10. 3390/polyml1121931.
Thiele et al. , uThe Current Status of Catalysis and Catalyst Development for the Industrial Process of Poly(ethylene terephthalate ) Polycondensation, https://doi.Org/10.1080/00914030108035115.

* cited by examiner

*Primary Examiner* — Pancham Bakshi
(74) *Attorney, Agent, or Firm* — Rahman LLC

(57) ABSTRACT

The present disclosure relates to a process for production of bis(2-hydroxyethyl) terephthalate (BHET) from polyethylene terephthalate (PET) comprising: (a) effecting partial depolymerization of PET by mixing PET with ethylene glycol in a weight ratio ranging from 1:0.3 to 1:1.5 maintaining temperature of the mixture in a range of 200° C. to 250° C. to obtain a partially depolymerized PET; and (b) effecting depolymerization of the partially depolymerized PET by contacting the partially depolymerized PET with ethylene glycol in a weight ratio of PET:ethylene glycol ranging from 1:1 to 1:4 in presence of a depolymerization catalyst at a temperature ranging from 170° C. to 200° C. for a time period ranging from 2 hours to 5 hours to produce a crude product mixture comprising bis(2-hydroxyethyl) terephthalate (BHET). The present disclosure also provides a process for recycling of PET from PET waste.

20 Claims, 4 Drawing Sheets

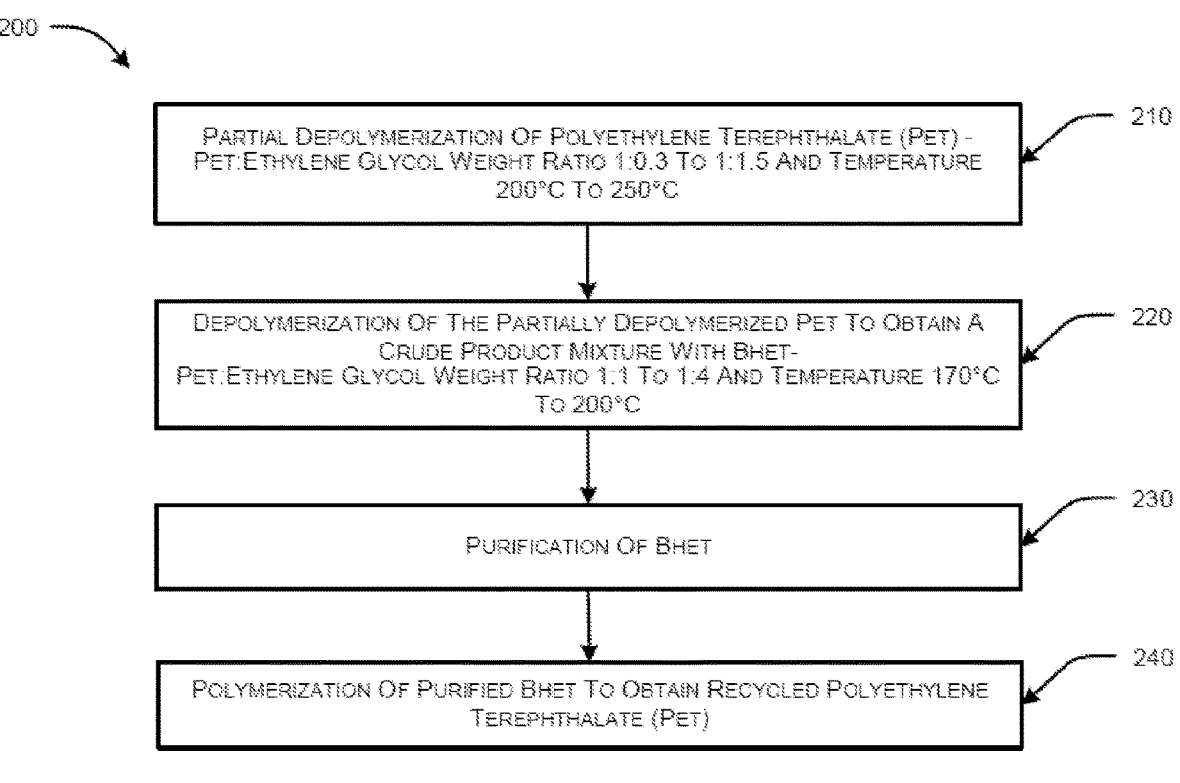

200

PARTIAL DEPOLYMERIZATION OF POLYETHYLENE TEREPHTHALATE (PET) -
PET:ETHYLENE GLYCOL WEIGHT RATIO 1:0.3 TO 1:1.5 AND TEMPERATURE
200°C TO 250°C                                                    — 210

DEPOLYMERIZATION OF THE PARTIALLY DEPOLYMERIZED PET TO OBTAIN A
CRUDE PRODUCT MIXTURE WITH BHET-
PET:ETHYLENE GLYCOL WEIGHT RATIO 1:1 TO 1:4 AND TEMPERATURE 170°C
TO 200°C                                                         — 220

PURIFICATION OF BHET                                              — 230

POLYMERIZATION OF PURIFIED BHET TO OBTAIN RECYCLED POLYETHYLENE
TEREPHTHALATE (PET)                                              — 240

MELT POLYETHYLENE TEREPHTHALATE (PET) AT TEMPERATURE RANGING FROM
240°C TO 330°C                                                   — 211

CONTACTING THE MOLTEN POLYETHYLENE TEREPHTHALATE (PET) WITH HOT
ETHYLENE GLYCOL AT A WEIGHT RATIO 1:0.3 TO 1:1.5, OPTIONALLY, IN
PRESENCE OF A DEPOLYMERIZATION CATALYST                          — 212

PARTIALLY DEPOLYMERIZED PET

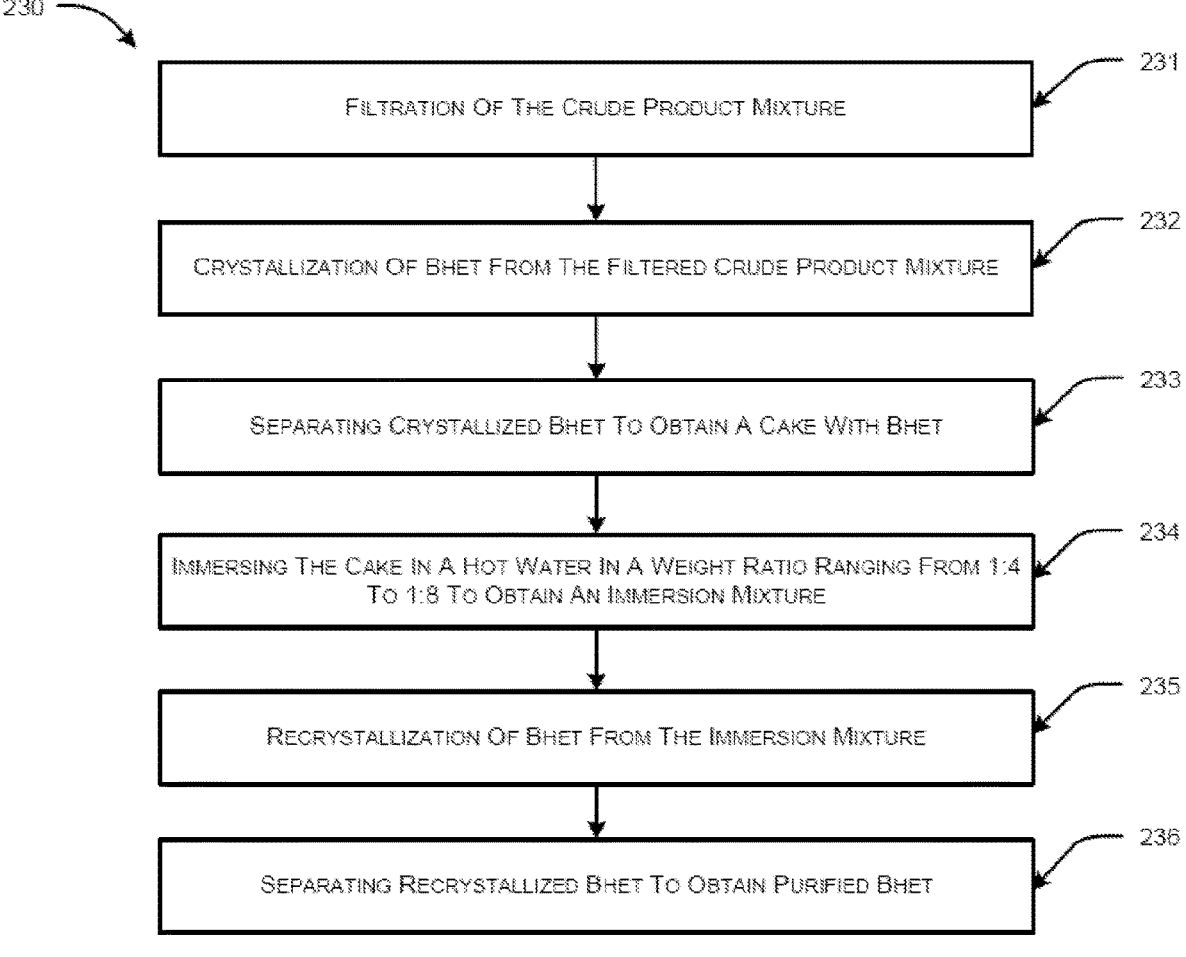

231
FILTRATION OF THE CRUDE PRODUCT MIXTURE

232
CRYSTALLIZATION OF BHET FROM THE FILTERED CRUDE PRODUCT MIXTURE

233
SEPARATING CRYSTALLIZED BHET TO OBTAIN A CAKE WITH BHET

234
IMMERSING THE CAKE IN A HOT WATER IN A WEIGHT RATIO RANGING FROM 1:4 TO 1:8 TO OBTAIN AN IMMERSION MIXTURE

235
RECRYSTALLIZATION OF BHET FROM THE IMMERSION MIXTURE

236
SEPARATING RECRYSTALLIZED BHET TO OBTAIN PURIFIED BHET

FIG. 5

PROCESS FOR RECYCLING OF POLYETHYLENE TEREPHTHALATE (PET) WASTE

CROSS REFERENCE TO RELATED APPLICATIONS

This application is a national stage application under 35 U.S.C. § 371 of PCT/IB2022/050519, filed Jan. 21, 2022, which claims priority from Indian Patent Application No. IN202121024616, filed Jun. 2, 2021, the entirety of which are expressly incorporated herein by reference.

TECHNICAL FIELD

The present disclosure generally relates to the field of recycling of plastic waste including, but not limited to flakes, polymers and post-consumer recycled plastic. More specifically, the present disclosure relates to a process for 5 recycling of polyethylene terephthalate (PET) waste. Another aspect of the present disclosure relates to a process for production of bis(2-hydroxyethyl) terephthalate (BHET) from polyethylene terephthalate (PET).

BACKGROUND

Background description includes information that may be useful in understanding the present invention, and each reference cited herein is expressly incorporated herein by reference in its entirety. It is not an admission that any of the information provided herein is prior-art or relevant to the presently claimed invention, or that any publication specifically or implicitly referenced is prior art.

Millions of tons of plastic waste are produced every year in 15 manufacturing of various products. A significant proportion of the plastic waste is accounted for by polyester waste such as PET bottles, thermoformed packages, polyester fiber, yarn and fabric waste and the likes. Rigorous research has been done, at least in the last 2 decades, in the area of polyester recycling to effectively make use of such recycled polyester in various applications.

One of the method that finds limited industrial utility in recycling of plastic waste, particularly, polyester waste is conversion thereof into monomers by deglycol reaction (also known as deglycolization reaction) i.e., reacting the polymer at a temperature of about 250° C. or more and at a pressure of 1 mmHg or less in presence of deglycol catalyst such as a metal compound catalyst to form 25 the monomers and then converting them into polymers to produce different kind of yarns.

Hu et al. in "Synthesis of poly(ethylene terephthalate) based on glycolysis of waste PET fiber", Journal of Macromolecular Science, Part A; Pure and Applied; Chemistry; Volume 57, 2020—Issue 6 (doi.org/10.1080/10601325.2019.1709498) discloses glycolysis as a chemical recycling route for waste poly(ethylene terephthalate) (PET), wherein glycolysis of waste PET fiber was carried out under nitrogen atmospheric condition with excess ethylene glycol (EG) as glycolysis agent and zinc acetate (Zn(Ac)2) as catalyst, contents whereof is incorporated herein in its entirety by way of reference.

US20040182782A1 discloses a method of obtaining BHET of high purity efficiently from an EG (ethylene glycol) solution containing crude BHET (bis(2-hydroxyethyl) terephthalate), especially a decomposition product solution obtained by decomposing a polyester containing PET (polyethylene terephthalate) as a main component, by use of EG, while minimizing by-production of impurity components such as DEG (diethylene glycol). DEG ester and oligomers, contents whereof is incorporated herein in its entirety by way of reference.

CN107266664A discloses a kind of reclaim of PET scrap technique, which is related to resource regeneration field, solves the recovery problem of colored polyester waste material, comprise the following steps: S1, pet waste crashed, cleans, dry. It is complete that S2, pet waste and EG, catalyst add depolymerization reaction under reactor, 170~210 DEG C. of constant temperature; S3, 125~145 DEG C. are cooled to, heat filtering obtains first-time filtrate and unreacted PET; S4, first-time filtrate distillation obtain EG; Liquid after S5, distillation adds solvent, and heat filtering obtains secondary filtrate and BHET oligomer; Added in S6, secondary filtrate and three filtrates are obtained after decolorising agent, heat filtering; S7, three filtrate crystallisation by cooling separate out acicular crystal, are filtrated to get monomer BHET, and in 60 DEG C. of dryings; Final minification gathers under precondensation under the conditions of S8, low vacuum, high vacuum condition; S9, Cast Strip, cooling, pelletizing and drying, finally obtain PET grain products, contents whereof is incorporated herein in its entirety by way of reference.

EP0723951A1 discloses a process to prepare very high purity bis(2-hydroxyethyl) terephthalate, using waste polyethylene terephthalate (PET) as the starting product. More specifically, the process is used to prepare BHET through the reaction of waste PET with excess ethylene glycol (EG), and preferably at a temperature of 190-210° C., in the presence of a transesterification catalyzer. This is followed by a series of separations and crystallisations (for which three different methods are proposed) to obtain a pure, chemically defined product that does not contain any of the impurities that may be found in the starting PET, contents whereof is incorporated herein in its entirety by way of reference.

Despite of rigorous research in the instant field for close to 50 years or so, glycolysis, as a method of regeneration or recycling of PET waste finds limited industrial utility owing to several drawbacks including—the process being energy intensive, time consuming and labor intensive, making it economically non-viable. Further, the conventional processes require large amounts of ethylene glycol and/or costly catalysts, which may pose environmental concerns.

There is, therefore, a need in the art to develop a relatively simple, safe, environmentally benign (or environment friendly) and cost-effective process for production of bis(2-hydroxyethyl) terephthalate (BHET) from polyethylene terephthalate (PET) that can alleviate or preclude one or more shortcomings of the conventional methods. Need is also felt of a process for recycling of polyethylene terephthalate (PET) waste.

SUMMARY AND OBJECTS OF THE INVENTION

An object of the present disclosure is to provide a process for production of bis(2-hydroxyethyl) terephthalate (BHET) from polyethylene terephthalate (PET) that can alleviate or preclude one or more shortcomings of the conventional methods.

Another object of the present disclosure is to provide a process for production of bis(2-hydroxyethyl) terephthalate (BHET) from polyethylene terephthalate (PET) that is relatively simple, safe, environment friendly and cost-effective.

Another object of the present disclosure is to provide a process for production of bis(2-hydroxyethyl) terephthalate (BHET) from polyethylene terephthalate (PET) that affords depolymerization of PET at a significantly reduced amounts of ethylene glycol.

Another object of the present disclosure is to provide a process for production of bis(2-hydroxyethyl) terephthalate (BHET) from polyethylene terephthalate (PET) that affords depolymerization of PET at reduced amounts of depolymerization catalyst.

Another object of the present disclosure is to provide a process for production of bis(2-hydroxyethyl) terephthalate (BHET) from polyethylene terephthalate (PET) that affords depolymerization of PET within short time period as compared to conventional processes.

Further object of the present disclosure is to provide a process for recycling of polyethylene terephthalate (PET) from polyethylene terephthalate (PET) waste.

Still further object of the present disclosure is to provide a process for recycling of polyethylene terephthalate (PET) from polyethylene terephthalate (PET) waste that is significantly economical, relatively simple, environment friendly and capable of implementation at an industrial scale.

The present disclosure generally relates to the field of recycling of plastic waste including, but not limited to flakes, polymers and post-consumer recycled plastic. The present disclosure is on the premise of a surprising observation by inventors of the instant application that when polyethylene terephthalate (PET) is subjected to partial depolymerization before it is subjected to depolymerization, it affords production of bis(2-hydroxyethyl) terephthalate (BHET) with higher yield, significantly reduced usage of ethylene glycol and/or significantly reduced usage of depolymerization catalyst, while reducing the time required for effecting depolymerization of polyethylene terephthalate (PET).

Accordingly, an aspect of the present disclosure relates to a process for production of bis(2-hydroxyethyl) terephthalate (BHET) from polyethylene terephthalate (PET), said process comprising the steps of: (a) effecting partial depolymerization of the polyethylene terephthalate (PET) by mixing the polyethylene terephthalate (PET) with ethylene glycol in a weight ratio of PET:ethylene glycol ranging from 1:0.3 to 1:1.5 maintaining temperature of the mixture in a range of 200° C. to 250° C. to obtain partially depolymerized polyethylene terephthalate (PET); and (b) effecting depolymerization of the partially depolymerized polyethylene terephthalate (PET) by contacting the partially depolymerized polyethylene terephthalate (PET) with ethylene glycol in a weight ratio of PET:ethylene glycol ranging from 1:1 to 1:4 in presence of a depolymerization catalyst at a temperature ranging from 170° C. to 200° C. for a time period ranging from 2 hours to 5 hours to produce crude product mixture comprising bis(2-hydroxyethyl) terephthalate (BHET). In an embodiment, the depolymerization catalyst is selected from a metal based catalyst, said metal being any of zinc, titanium and antimony.

In an embodiment, the polyethylene terephthalate (PET) comprises polyethylene terephthalate (PET) waste selected from PET bottle flakes, PET yarn, PET thermoformed packages. PET fabric, bright PET yam waste popcorn, semi dull PET yarn waste popcorn and mixtures thereof. In an embodiment, the polyethylene terephthalate (PET) comprises polyethylene terephthalate (PET) waste having an intrinsic viscosity ranging from 0.5 to 0.8, melting point ranging from 240° C. to 260° C. and ash content ranging from 0.03% to 2.0% by weight.

In an embodiment, the step of partial depolymerization of polyethylene terephthalate (PET) comprises: (a) exposing polyethylene terephthalate (PET) to a temperature ranging from 240° V to 330° C. to obtain molten polyethylene terephthalate (PET); and (b) contacting the molten polyethylene terephthalate (PET) with hot ethylene glycol in a weight ratio of PET:ethylene glycol ranging from 1:0.3 to 1:1.5 to obtain partially depolymerized polyethylene terephthalate (PET). In an embodiment, the molten polyethylene terephthalate (PET) is contacted with hot ethylene glycol in presence of a depolymerization catalyst. In an embodiment, the molten polyethylene terephthalate (PET) is contacted with hot ethylene glycol in presence of zinc acetate in an amount ranging from 200 ppm to 800 ppm. In an embodiment, the hot ethylene glycol has a temperature ranging from 180° C. to 190° C. In an embodiment, the partially depolymerized polyethylene terephthalate (PET) is contacted with ethylene glycol in presence of zinc acetate in an amount ranging from 400 ppm to 1400 ppm.

Another aspect of the present disclosure relates to a process for recycling of polyethylene terephthalate (PET) from polyethylene terephthalate (PET) waste, said process comprising the steps of: (a) effecting partial depolymerization of the polyethylene terephthalate (PET) waste by mixing the polyethylene terephthalate (PET) waste with ethylene glycol in a weight ratio of PET:ethylene glycol ranging from 1:0.3 to 1:1.5 maintaining temperature of the mixture in a range of 200° C. to 250° C. to obtain a partially depolymerized polyethylene terephthalate (PET); (b) effecting depolymerization of the partially depolymerized polyethylene terephthalate (PET) by contacting the partially depolymerized polyethylene terephthalate (PET) with ethylene glycol in a weight ratio of PET:ethylene glycol ranging from 1:1 to 1:4 in presence of a depolymerization catalyst at a temperature ranging from 170° C. to 200° C. for a time period ranging from 2 hours to 5 hours to produce a crude product mixture comprising bis(2-hydroxyethyl) terephthalate (BHET); (c) subjecting the crude product mixture to a step of purification to obtain purified bis(2-hydroxyethyl) terephthalate (BHET); and (d) effecting polymerization of the purified bis(2-hydroxyethyl) terephthalate (BHET) in presence of a polymerization catalyst at a temperature ranging from 200° C. to 300° C. at a pressure ranging from 50 mbar to 2 mbar for a time period ranging from 2 hours to 5 hours to obtain the recycled polyethylene terephthalate (PET). In an embodiment, the polymerization catalyst is selected from Antimony Trioxide, Antimony Triacetate, Antimony Glycolate, and Germanium Dioxide. In an embodiment, the polyethylene terephthalate (PET) waste is selected from PET bottle flakes, bright PET yarn, bright PET yam waste popcorn, semi dull PET yarn waste popcorn and mixtures thereof having an intrinsic viscosity ranging from 0.5 to 0.8, melting point ranging from 240° C. to 260° C. and ash content ranging from 0.03% to 2.0%.

In an embodiment, the step of partial depolymerization of the polyethylene terephthalate (PET) waste comprises: (a) exposing polyethylene terephthalate (PET) waste to a temperature ranging from 240° C. to 330° C. to obtain molten polyethylene terephthalate (PET); and (b) contacting the molten polyethylene terephthalate (PET) with hot ethylene glycol in a weight ratio ranging from 1:0.3 to 1:1.5 to obtain partially depolymerized polyethylene terephthalate (PET).

In an embodiment, the molten polyethylene terephthalate (PET) is contacted with hot ethylene glycol a temperature ranging from 180° C. to 190° C. in presence of zinc acetate in an amount ranging from 200 ppm to 800 ppm. In an embodiment, the partially depolymerized polyethylene terephthalate (PET) is contacted with ethylene glycol in presence of zinc acetate in an amount ranging from 400 ppm to 1400 ppm. In an embodiment, the polymerization catalyst is selected from Antimony Trioxide, Antimony Triacetate, Antimony Glycolate, and Germanium Dioxide.

In an embodiment, the step of purification of the crude product mixture comprises: effecting filtration of the crude product mixture; effecting crystallization of bis(2-hydroxyethyl) terephthalate (BHET) from the filtered crude product mixture; separating crystallized bis(2-hydroxyethyl) terephthalate (BHET) to obtain a cake comprising bis(2-hydroxyethyl) terephthalate (BHET); immersing the cake in a hot water in a weight ratio ranging from 1:4 to 1:8 to obtain an immersion mixture, said hot water having temperature ranging from 90° C. to 98° C.; effecting recrystallization of bis(2-hydroxyethyl) terephthalate (BHET) from the immersion mixture; and separating recrystallized bis(2-hydroxyethyl) terephthalate (BHET) to obtain purified bis(2-hydroxyethyl) terephthalate (BHET).

BRIEF DESCRIPTION OF DRAWINGS

FIG. 3 illustrates an exemplary flow chart depicting a process for recycling of polyethylene terephthalate (PET) from polyethylene terephthalate (PET) waste, in accordance with an embodiment of the present disclosure.

FIG. 4 illustrates an exemplary flow chart depicting details of the step (210) of effecting partial depolymerization of the polyethylene terephthalate (PET), in accordance with an embodiment of the present disclosure.

FIG. 5 illustrates an exemplary flow chart depicting details of the step (230) of purification of the crude product mixture, in accordance with an embodiment of the present disclosure.

DETAILED DESCRIPTION OF THE PREFERRED EMBODIMENTS

Figure 1:
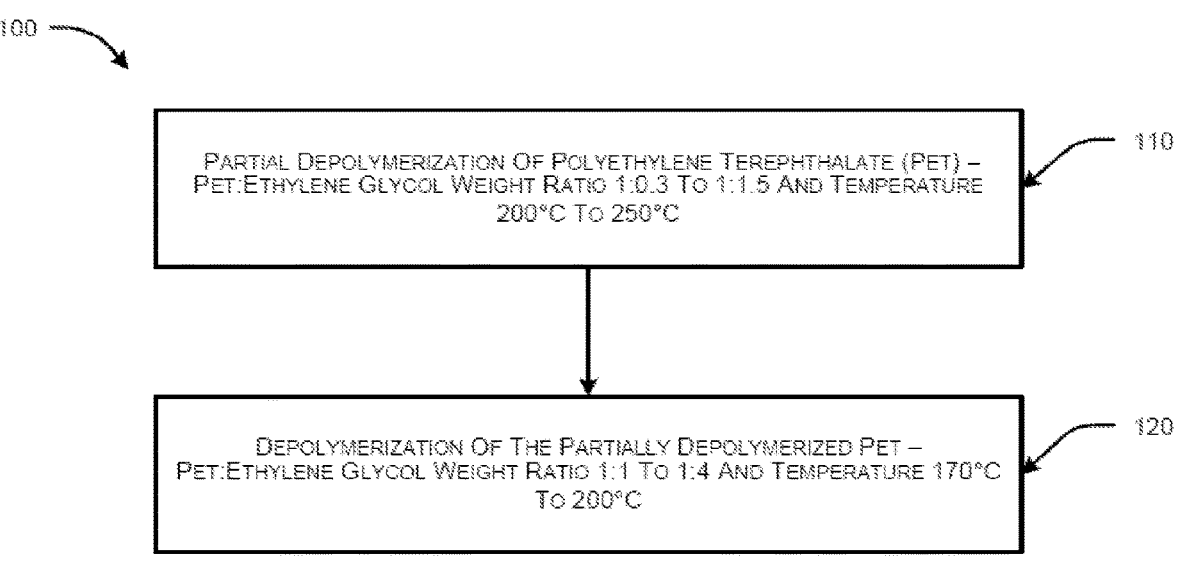
FIG. 1 illustrates an exemplary flow chart depicting a process for production of bis(2-hydroxyethyl) terephthalate (BHET) from polyethylene terephthalate (PET), in accordance with an embodiment of the present disclosure.

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The present disclosure generally relates to the field of recycling of plastic waste including, but not limited to flakes, polymers and post-consumer recycled plastic. More specifically, the present disclosure relates to a process for recycling of polyethylene terephthalate (PET) waste. Another aspect of the present disclosure relates to a process for production of bis(2-hydroxyethyl) terephthalate (BHET) from polyethylene terephthalate (PET).

Various terms as used herein are shown below. To the extent a term used in a claim is not defined below, it should be given the broadest definition persons in the pertinent art have given that term as reflected in printed publications and issued patents at the time of filing.

The terms "polyethylene terephthalate (PET)", "polyethylene terephthalate (PET) waste" and "plastic waste" as used herein throughout the present disclosure synonymously and interchangeably denotes the meaning of pieces, particles or particulate matters, either in the solid form or in semi solid/viscous form, of any dimensions, primarily composed of polyethylene terephthalate (PET) that may serve as a source of the polymeric material that may be subjected to advantageous process of the present disclosure. Examples of polyethylene terephthalate (PET) based polymers or polymeric materials that may be subjected to the process of the instant disclosure includes, but not limited to, PET based refused products, wastes generated during production of PET products, industrial PET based waste, consumer led PET based plastic wastes such as municipal plastic wastes, and PET based plastic wastes dumped at the landfill sites. When the process of the instant disclosure is implemented for regeneration of PET, that is particularly suitable for production of polyester yams, the polyethylene terephthalate (PET) (or plastic waste) may include PET bottle flakes, yarn waste, thermoformed packages, PET fabric, bright PET yam waste popcorn, semi dull PET yam waste popcorn and mixtures thereof; particularly suitable are those materials having an intrinsic viscosity ranging from 0.5 to 0.8, peak melting point ranging from 240° C. to 260° C., and Deg % ranging from 1.4 to 1.6. The polyester/PET yarn waste popcorn, as would be appreciated by the persons skilled in the art, can be prepared by converting the yarn waste to PET/polyester popcorns as known conventionally; such popcorns being suitable for feeding into the extruder.

The present disclosure is on the premise of a surprising observation by inventors of the instant application that when polyethylene terephthalate (PET) is subjected to partial depolymerization, before it is subjected to depolymerization, it affords production of bis(2-hydroxyethyl) terephthalate (BHET) with higher yield, significantly reduced usage of ethylene glycol and/or significantly reduced usage of depolymerization catalyst, while reducing the time required for effecting de polymerization of polyethylene terephthalate (PET).

Accordingly, an aspect of the present disclosure relates to a process for production of bis(2-hydroxyethyl) terephthalate (BHET) from polyethylene terephthalate (PET), said process comprising the steps of: (a) effecting partial depolymerization of the polyethylene terephthalate (PET) by mixing the polyethylene terephthalate (PET) with ethylene glycol in a weight ratio of PET:ethylene glycol ranging from 1:0.3 to 1:1.5 maintaining temperature of the mixture in a range of 200° C. to 250° C. to obtain partially depolymerized polyethylene terephthalate (PET); and (b) effecting depolymerization of the partially depolymerized polyethylene terephthalate (PET) by contacting the partially depolymerized polyethylene terephthalate (PET) with ethylene glycol in a weight ratio of PET:ethylene glycol ranging from 1:1 to 1:4 in presence of a depolymerization catalyst at a temperature ranging from 170° C. to 200° C. for a time period ranging from 2 hours to 5 hours to produce crude product mixture comprising bis(2-hydroxyethyl) terephthalate (BHET). In an embodiment, the depolymerization catalyst is selected from a metal based catalyst, said metal being any of zine, titanium and antimony.

FIG. 1 illustrates an exemplary flow chart depicting a process for production of bis(2-hydroxyethyl) terephthalate (BHET) from polyethylene terephthalate (PET), in accordance with an embodiment of the present disclosure. As can be seen from FIG. 1, the process includes: at step 110, effecting partial depolymerization of the polyethylene terephthalate (PET) by mixing the polyethylene terephthalate (PET) with ethylene glycol in a weight ratio of PET:ethylene glycol ranging from 1:0.3 to 1:1.5, preferably, ranging from 1:0.3 to 1:1 and most preferably, ranging from 1:0.4 to 1:0.7 maintaining temperature of the mixture in a range of 200° C. to 250° C. to obtain partially depolymerized polyethylene terephthalate (PET), and at step 120, effecting depolymerization of the partially depolymerized polyethylene terephthalate (PET) by contacting the partially depolymerized polyethylene terephthalate (PET) with ethylene glycol in a weight ratio of PET:ethylene glycol ranging from 1:1 to 1:4, preferably, ranging from 1:2 to 1:4 and most preferably, ranging from 1:2.5 to 1:3.5 in presence of a depolymerization catalyst at a temperature ranging from 170° C. to 200° C. for a time period ranging from 2 hours to 5 hours to produce a crude product mixture comprising bis(2-hydroxyethyl) terephthalate (BHET).

In an embodiment, the step of partial depolymerization of polyethylene terephthalate (PET) comprises: (a) exposing polyethylene terephthalate (PET) to a temperature ranging from 240° C. to 330° C. to obtain molten polyethylene terephthalate (PET); and (b) contacting the molten polyethylene terephthalate (PET) with hot ethylene glycol in a weight ratio of PET:ethylene glycol ranging from 1:0.3 to 1:1.5 to obtain partially depolymerized polyethylene terephthalate (PET).

Figure 2:
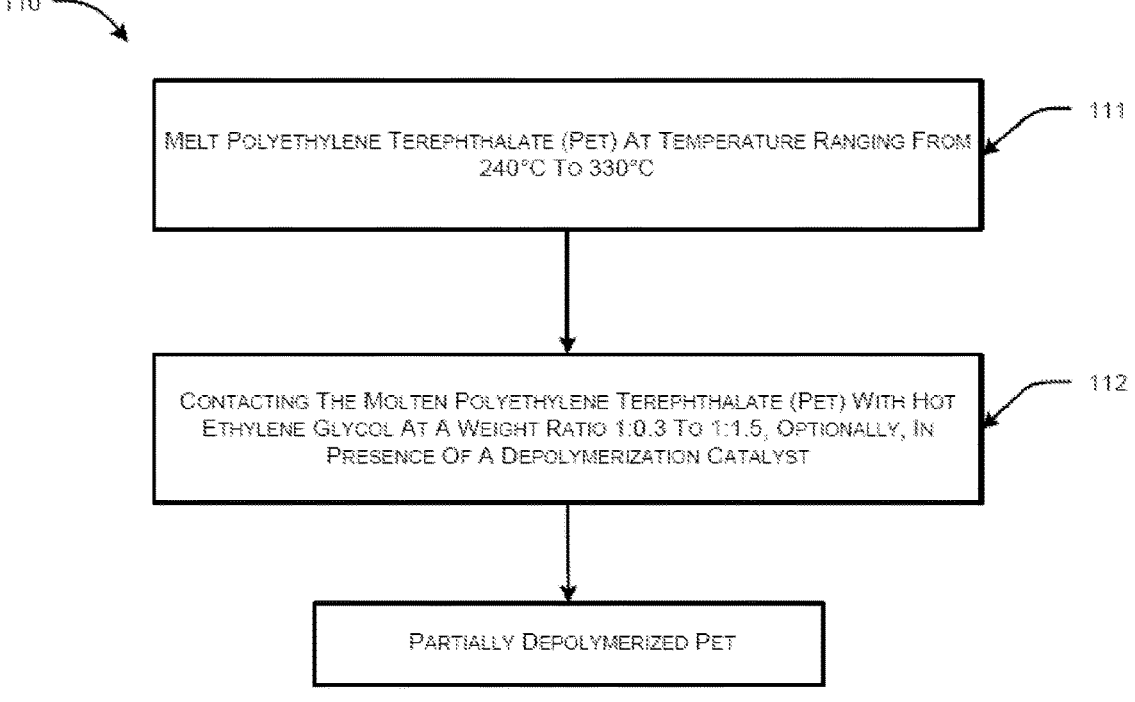
FIG. 2 illustrates an exemplary flow chart depicting details of the step (110) of effecting partial depolymerization of the polyethylene terephthalate (PET), in accordance with an embodiment of the present disclosure.

FIG. 2 illustrates an exemplary flow chart depicting details of the step (110) of effecting partial depolymerization of the polyethylene terephthalate (PET), in accordance with an embodiment of the present disclosure. As can be seen from FIG. 2, at step 111, polyethylene terephthalate (PET) is exposed to a temperature ranging from 240° C. to 330° C. to obtain molten polyethylene terephthalate (PET), and at step 112, the molten polyethylene terephthalate (PET) is contacted with hot ethylene glycol in a weight ratio of PET:ethylene glycol ranging from 1:0.3 to 1:1.5 to obtain partially depolymerized polyethylene terephthalate (PET).

In an embodiment, the molten polyethylene terephthalate (PET) is contacted with hot ethylene glycol in presence of a depolymerization catalyst. The depolymerization catalyst may be any metal based depolymerization catalyst such as salts or oxides of Zn, Sb, Ti, Mn, Na, K and the likes. Non-limiting examples of depolymerization catalyst suitable for the process of the present disclosure are zinc acetate, sodium carbonate, sodium bicarbonate, sodium sulphate and potassium sulphate. In an embodiment, the molten polyethylene terephthalate (PET) is contacted with hot ethylene glycol in presence of zinc acetate in an amount ranging from 200 ppm to 800 ppm. In an embodiment, the hot ethylene glycol has a temperature ranging from 180° C. to 190° C. In an embodiment, the partially depolymerized polyethylene terephthalate (PET) is contacted with ethylene glycol in presence of zinc acetate in an amount ranging from 400 ppm to 1400 ppm.

In an embodiment, the polyethylene terephthalate (PET) includes polyethylene terephthalate (PET) waste selected from PET bottle flakes. PET yam. PET thermoformed packages, PET fabric, bright PET yam waste popcorn, semi dull PET yam waste popcorn and mixtures thereof. In an embodiment, the polyethylene terephthalate (PET) comprises polyethylene terephthalate (PET) waste having an intrinsic viscosity ranging from 0.5 to 0.8, peak melting point ranging from 240° C. to 260° C. and ash content ranging from 0.03% to 2.0%.

In an embodiment, polyethylene terephthalate (PET) waste may be subjected to pre-processing as conventionally known to a person skilled in the art. For example, the PET waste may be subjected to sorting, removal of impurities such as dirt, foreign materials, color materials and the likes, size reduction, cleaning and drying. In an exemplary instance, the polyester (PET) bottles are collected and sorted to remove PVC contents such as caps and name wrappers. Separated PET bottles are then cleaned with water wash and dried, and then cut into small flakes with the help of cutter. Alternatively, waste PET flakes can directly be procured from the market and be sorted for removal of foreign contaminations. Then it is washed through washing line. Water is separated and excess/un-bound moisture is removed through dryer. This pre-processed polyethylene terephthalate (PET) can then be subjected to further processing in accordance with embodiments of the present disclosure to produce bis(2-hydroxyethyl) terephthalate (BHET) and/or regenerated/recycled polyethylene terephthalate (PET).

The polyethylene terephthalate (PET) may be fed to an extruder to effect melting of the polyethylene terephthalate (PET). Any conventional extruder that includes one or more heating zones and conveyer(s) or other displacement mechanism(s) may be used. In an embodiment, the polyethylene terephthalate (PET) is exposed to a temperature ranging from 240° C. to 330° C. to obtain molten polyethylene terephthalate (PET). In an embodiment, the polyethylene terephthalate (PET) is exposed to a temperature ranging from 280° C. to 300° C. to obtain molten polyethylene terephthalate (PET).

The molten polyethylene terephthalate (PET) is then contacted with ethylene glycol, optionally, in presence of a depolymerization catalyst to effect partial depolymerization thereof. In an embodiment, the molten polyethylene terephthalate (PET) is contacted with hot ethylene glycol without usage of the depolymerization catalyst. In an embodiment, the molten polyethylene terephthalate (PET) is contacted with hot ethylene glycol at a weight ratio of PET:ethylene glycol ranging from 1:0.3 to 1:1.5, preferably, ranging from 1:0.3 to 1:1 and most preferably, ranging from 1:0.4 to 1:0.7.

In an embodiment, the molten polyethylene terephthalate (PET) is contacted with hot ethylene glycol in presence of a depolymerization catalyst. In an embodiment, the depolymerization catalyst is selected from a metal based catalyst, said metal being any of zinc, titanium and antimony. In an embodiment, the depolymerization catalyst is selected from zinc acetate, sodium carbonate, sodium bicarbonate, sodium sulphate and potassium sulphate. In an embodiment, the molten polyethylene terephthalate (PET) is contacted with hot ethylene glycol in presence of zinc acetate in an amount ranging from 200 ppm to 800 ppm. In an embodiment, the molten polyethylene terephthalate (PET) is contacted with hot ethylene glycol in presence of zinc acetate in an amount ranging from 300 ppm to 600 ppm. In an embodiment, the molten polyethylene terephthalate (PET) is contacted with hot ethylene glycol in presence of zinc acetate in an amount of about 500 ppm.

In an embodiment, the hot ethylene glycol has a temperature ranging from 150° C. to 200° C., preferably, has a temperature ranging from 170° C. to 200° C., more preferably, has a temperature ranging from 180° C. to 190° C. and most preferably, has a temperature ranging from 188° C. to 190° C.

In an embodiment, desired amount(s) of the hot ethylene glycol (and optionally, the catalyst) are injected in the line carrying the molten polyethylene terephthalate (PET) to a reactor at one or more places for effecting partial de polymerization thereof. Alternatively, the molten polyethylene terephthalate (PET) can be contacted with hot ethylene glycol (optionally, in presence of the catalyst) in a separate reactor to effect partial depolymerization thereof. Since the molten polyethylene terephthalate (PET) has a temperature ranging from 240° C. to 330° C., the hot ethylene glycol, immediately upon coining in contact with the molten polyethylene terephthalate (PET), goes into the vapor state partially depolymerizing the molten polyethylene terephthalate (PET).

The partially depolymerized polyethylene terephthalate (PET) is then fed to a reactor for effecting depolymerization thereof, wherein the partially depolymerized polyethylene terephthalate (PET) is contacted with ethylene glycol in a weight ratio of PET:ethylene glycol ranging from 1:1 to 1:4, preferably, ranging from 1:2 to 1:4 and most preferably, ranging from 1:2.5 to 1:3.5 in presence of a depolymerization catalyst selected from a metal based catalyst, said metal being any of zinc, titanium and antimony at a temperature ranging from 170° C. to 200° C. for a time period ranging from 2 hours to 5 hours to produce a crude product mixture comprising bis(2-hydroxyethyl) terephthalate (BHET).

In an embodiment, the partially depolymerized polyethylene terephthalate (PET) is contacted with ethylene glycol at a temperature ranging from 190° C. to 200° C. In an embodiment, the partially depolymerized polyethylene terephthalate (PET) is contacted with ethylene glycol at a temperature ranging from 195° C. to 200° C.

In an embodiment, the partially depolymerized polyethylene terephthalate (PET) is contacted with ethylene glycol in presence of zinc acetate in an amount ranging from 400 ppm to 1400 ppm. In an embodiment, the partially depolymerized polyethylene terephthalate (PET) is contacted with ethylene glycol in presence of zinc acetate in an amount ranging from 400 ppm to 1000 ppm. In an embodiment, the partially depolymerized polyethylene terephthalate (PET) is contacted with ethylene glycol in presence of zinc acetate in an amount ranging from 400 ppm to 600 ppm. In an embodiment, the partially depolymerized polyethylene terephthalate (PET) is contacted with ethylene glycol in presence of zinc acetate in an amount of about 500 ppm.

The crude product mixture comprising bis(2-hydroxyethyl) terephthalate (BHET) may further be subjected to further purification and/or separation process(es), as known in the state of art, to obtain bis(2-hydroxyethyl) terephthalate (BHET) of desired purity grade.

Another aspect of the present disclosure relates to a process for recycling of polyethylene terephthalate (PET) from polyethylene terephthalate (PET) waste, said process comprising the steps of: (a) effecting partial depolymerization of the polyethylene terephthalate (PET) waste by mixing the polyethylene terephthalate (PET) waste with ethylene glycol in a weight ratio of PET:ethylene glycol ranging from 1:0.3 to 1:1.5 maintaining temperature of the mixture in a range of 200° C. to 250° (C to obtain partially depolymerized polyethylene terephthalate (PET); (b) effecting depolymerization of the partially depolymerized polyethylene terephthalate (PET) by contacting the partially depolymerized polyethylene terephthalate (PET) with ethylene glycol in a weight ratio of PET:ethylene glycol ranging from 1:1 to 1:4 in presence of a depolymerization catalyst at a temperature ranging from 170° C. to 200° C. for a time period ranging from 2 hours to 5 hours to produce a crude product mixture comprising bis(2-hydroxyethyl) terephthalate (BHET); (c) subjecting the crude product mixture to a step of purification to obtain purified bis(2-hydroxyethyl) terephthalate (BHET); and (d) effecting polymerization of the purified bis(2-hydroxyethyl) terephthalate (BHET) in presence of a polymerization catalyst at a temperature ranging from 200° C. to 300° C. at a pressure ranging from 50 mbar to 5 mbar for a time period ranging from 2 hours to 5 hours to obtain the recycled polyethylene terephthalate (PET). In an embodiment, the depolymerization catalyst is selected from a metal based catalyst, said metal being any of zinc, titanium and antimony. In an embodiment, the depolymerization catalyst is selected from zinc acetate, sodium carbonate, sodium bicarbonate, sodium sulphate and potassium sulphate.

FIG. 3 illustrates an exemplary flow chart depicting a process for recycling of polyethylene terephthalate (PET) from polyethylene terephthalate (PET) waste, in accordance with an embodiment of the present disclosure. As can be seen from FIG. 3, the process includes: at step 210, effecting partial depolymerization of the polyethylene terephthalate (PET) waste by mixing the polyethylene terephthalate (PET) waste with ethylene glycol in a weight ratio of PET rethylene glycol ranging from 1:0.3 to 1:1.5, preferably, ranging from 1:0.3 to 1:1 and most preferably, ranging from 1:0.4 to 1:0.7 maintaining temperature of the mixture in a range of 200° C. to 250° C. to obtain partially depolymerized polyethylene terephthalate (PET), at step 220, effecting depolymerization of the partially depolymerized polyethylene terephthalate (PET) by contacting the partially depolymerized polyethylene terephthalate (PET) with ethylene glycol in a weight ratio of PET:ethylene glycol ranging from 1:1 to 1:4, preferably, ranging from 1:2 to 1:4 and most preferably, ranging from 1:2.5 to 1:3.5 in presence of a depolymerization catalyst at a temperature ranging from 170° C. to 200° C. for a time period ranging from 2 hours to 5 hours to produce a crude product mixture comprising bis(2-hydroxyethyl) terephthalate (BHET), at step 230, subjecting the crude product mixture to a step of purification to obtain purified bis(2-hydroxyethyl) terephthalate (BHET); and at step 240, effecting polymerization of the purified bis(2-hydroxyethyl) terephthalate (BHET) in presence of a polymerization catalyst at a temperature ranging from 200° C. to 300° C. and at a pressure ranging from 50 mbar to 5 mbar, preferably, at a pressure ranging from 50 mbar to 2 mbar for a time period ranging from 2 hours to 5 hours to obtain the recycled polyethylene terephthalate (PET).

In an embodiment, the polyethylene terephthalate (PET) waste is selected from PET bottle flakes, PET yarn. PET thermoformed packages, PET fabric, bright PET yarn waste popcorn, semi dull PET yarn waste popcorn and mixtures thereof having an intrinsic viscosity ranging from 0.5 to 0.8, melting point ranging from 240° C. to 260° C. and ash content ranging from 0.03% to 2.0%.

In an embodiment, the step of partial depolymerization of the polyethylene terephthalate (PET) waste comprises: (a) exposing polyethylene terephthalate (PET) waste to a temperature ranging from 240° C. to 330° C. to obtain molten polyethylene terephthalate (PET); and (b) contacting the molten polyethylene terephthalate (PET) with hot ethylene glycol in a weight ratio ranging from 1:0.3 to 1:1.5 to obtain partially depolymerized polyethylene terephthalate (PET). In an embodiment, the molten polyethylene terephthalate (PET) is contacted with hot ethylene glycol in presence of zinc acetate in an amount ranging from 200 ppm to 800 ppm.

FIG. 4 illustrates an exemplary flow chart depicting details of the step (210) of effecting partial depolymerization of the polyethylene terephthalate (PET), in accordance with an embodiment of the present disclosure. As can be seen from FIG. 4, at step 211, polyethylene terephthalate (PET) is exposed to a temperature ranging from 240° C. to 330° C. to obtain molten polyethylene terephthalate (PET), and at step 212, the molten polyethylene terephthalate (PET) is contacted with hot ethylene glycol in a weight ratio of PET:ethylene glycol ranging from 1:0.3 to 1:1.5, preferably, ranging from 1:0.3 to 1:1 and most preferably, ranging from 1:0.4 to 1:0.7 to obtain partially depolymerized polyethylene terephthalate (PET).

In an embodiment, the step of purification of the crude product mixture comprises: effecting filtration of the crude product mixture; effecting crystallization of bis(2-hydroxyethyl) terephthalate (BHET) from the filtered crude product mixture; separating crystallized bis(2-hydroxyethyl) terephthalate (BHET) to obtain a cake comprising bis(2-hydroxyethyl) terephthalate (BHET); immersing the cake in a hot water in a weight ratio ranging from 1:4 to 1:8 to obtain an immersion mixture, said hot water having temperature ranging from 90° C. to 98° C.; effecting recrystallization of bis(2-hydroxyethyl) terephthalate (BHET) from the immersion mixture; and separating recrystallized bis(2-hydroxyethyl) terephthalate (BHET) to obtain purified bis(2-hydroxyethyl) terephthalate (BHET).

FIG. 5 illustrates an exemplary flow chart depicting details of the step (230) of purification of the crude product mixture, in accordance with an embodiment of the present disclosure. As can be seen from FIG. 5, at step 231, filtration of the crude product mixture is effected, at step 232, crystallization of bis(2-hydroxyethyl) terephthalate (BHET) is effected from the filtered crude product mixture, at step 233, crystallized bis(2-hydroxyethyl) terephthalate (BHET) is separated to obtain a cake comprising bis(2-hydroxyethyl) terephthalate (BHET), at step 234, the cake is immersed in a hot water, having temperature ranging from 90° C. to 98° C. in a weight ratio ranging from 1:4 to 1:8 to obtain an immersion mixture, at step 235, bis(2-hydroxyethyl) terephthalate (BHET) is recrystallized from the immersion mixture, at step 236, the recrystallized bis(2-hydroxyethyl) terephthalate (BHET) is separated to obtain purified bis(2-hydroxyethyl) terephthalate (BHET).

With regards filtration of the crude product mixture, any conventional filtration assembly may be used for effecting filtration of the crude product mixture. In an embodiment, the crude product mixture comprising bis(2-hydroxyethyl) terephthalate (BHET) is passed through a mesh filter of 50 mesh to 150 mesh, preferably, of about 80 mesh to obtain a filtered mass. The filtered mass may then be cooled down to a temperature ranging from 70° C. to 130° C. In an embodiment, the filtered mass is cooled down to a temperature ranging from 80° C. to 100° C., preferably, at about 90° C. The cooled filtered mass can then be passed through one or more filtration units to obtain the filtered crude product mixture. In an embodiment, the cooled filtered mass is passed through a series of filters. The series of filter may include activated charcoal filter, cation exchange resin, anion exchange resin, diatomaceous earth filter and the likes. In an embodiment, the series of filters include: activated charcoal filter having bulk density ranging from 0.3 to 0.7 gm/cc, preferably, of about 0.5 gm/cc; a cation exchange resin; an anion exchange resin having chromium selective functional groups; and a diatomaceous earth filter having bulk density ranging from 0.2 to 0.4 gm/cc, preferably, of about 0.24 gm/cc. In an embodiment, the residence time of the crude product mixture during the filtration ranges from 10 minutes to 30 minutes.

The filtered crude product mixture is then subjected to crystallization to crystallize bis(2-hydroxyethyl) terephthalate (BHET) therefrom. Any crystallization technique as known to or appreciated by a person skilled in the art may be used. In an embodiment, the filtered crude product mixture is mixed with ethylene glycol in a weight ratio ranging from 1:1.5 to 1:5, preferably, in a weight ratio ranging from 1:1.7 to 1:3 and most preferably, in a weight ratio of about 1:2. The ethylene glycol may be recycled ethylene glycol. The resultant mixture is then cooled to a temperature ranging from 20° C. to 30° C. to effect crystallization of bis(2-hydroxyethyl) terephthalate (BHET).

The crystallized bis(2-hydroxyethyl) terephthalate (BHET) is then separated out to obtain a cake comprising bis(2-hydroxyethyl) terephthalate (BHET). Any conventional technique may be used for separation of crystallized bis(2-hydroxyethyl) terephthalate (BHET). In an embodiment, the cooled mixture containing crystallized bis(2-hydroxyethyl) terephthalate (BHET) is subjected to a filter press to separate out excess ethylene glycol and to obtain a cake having bis(2-hydroxyethyl) terephthalate (BHET). The cake may contain about 20% to 50% ethylene glycol by weight of the cake.

The cake is then immersed in a hot water in a weight ratio ranging from 1:4 to 1:8 to obtain an immersion mixture. The hot water can have a temperature ranging from 90° C. to 98° C. The immersion mixture may be subjected to filtration, for example, by using a non-woven filter. The filtered immersion mixture can then be cooled down to a temperature ranging from 20° C. to 30° C., preferably, at about 22° C. and water is added to the cooled mixture to effect recrystallization of bis(2-hydroxyethyl) terephthalate (BHET).

The recrystallized bis(2-hydroxyethyl) terephthalate (BHET) is then separated out to obtain purified bis(2-hydroxyethyl) terephthalate (BHET). Any conventional technique may be used for separation of recrystallized bis(2-hydroxyethyl) terephthalate (BHET). In an embodiment, the cooled mixture containing recrystallized bis(2-hydroxyethyl) terephthalate (BHET) is subjected to a filter press to separate out excess water and to obtain a cake having purified bis(2-hydroxyethyl) terephthalate (BHET). The cake having purified bis(2-hydroxyethyl) terephthalate (BHET) may contain about 20% to 50% water and 5% to 15% ethylene glycol by weight of the cake.

The purified BHET so obtained can then be subjected to polymerization to obtain recycled PET. Polymerization of BHET to PET is well known in the state-of-art and the same may be used. In an embodiment, the purified bis(2-hydroxy-ethyl) terephthalate (BHET) is polymerized in presence of a polymerization catalyst at a temperature ranging from 200° C. to 300° C. at a pressure ranging from 50 mbar to 5 mbar for a time period ranging from 2 hours to 5 hours to obtain the recycled polyethylene terephthalate (PET).

Any polymerization catalyst, as known to persons skilled in the ail may be used. A list of exemplary polymerization catalysts may be found in journal articles—Kim et al., "Effect of Polycondensation Catalyst on Fiber Structure Development in High-Speed Melt Spinning of Poly (Ethylene Terephthalate Polymers 2019, 11, 1931; doi:10.3390/polyml 1121931; and Thiele et al., "7¾e Current Status of Catalysis and Catalyst Development for the Industrial Process of Poly(ethylene terephthalate) Polycondensation", doi.Org/10.1080/00914030108035115. In an embodiment, the polymerization catalyst is selected from Antimony Trioxide. Antimony Triacetate. Antimony Glycolate, Germanium Dioxide or any other Titanium or Aluminium based catalysts. In an embodiment, the polymerization catalyst is selected from Antimony Trioxide. Antimony Triacetate, Antimony Glycolate, and Germanium Dioxide.

In an embodiment, the purified BHET is melted and the molten BHET is charged in a reactor along with the polymerization catalyst and the reactor temperature is set at a temperature ranging from 190° C. to 230° C. preferably, at about 210° C. and vacuum is applied (e.g., about 800 mbar) that may aid in removal of moisture and any ethylene glycol that may be present therein. Temperature of the reactor can then be increased to a desired temperature, for example, to about 270° C. and vacuum can be applied at a desired pressure, for example, at about 20 mbar over a period of 1 hour to 3 hours. Under these temperature and vacuum conditions, the BHET gets partially polymerized. The partially polymerized reaction mixture can then be subjected to a temperature ranging from 260° C. to 300° C. preferably, at about 275° C. and to a vacuum at a pressure ranging from 1 mbar to 4 mbar, preferably, at about 2 mbar for a time period ranging from 1 hour to 2 hours. Torque may be measured during the course of reaction to monitor the progress of the reaction, and when the desired torque value is obtained, the reaction is stopped. The recycled PET may then, optionally, be fed to a cutter to obtain recycled PET chips. The recycled PET (and the recycled PET chips) so obtained in accordance with embodiments of the present disclosure is particularly suitable for production of yarns.

Figure 6:
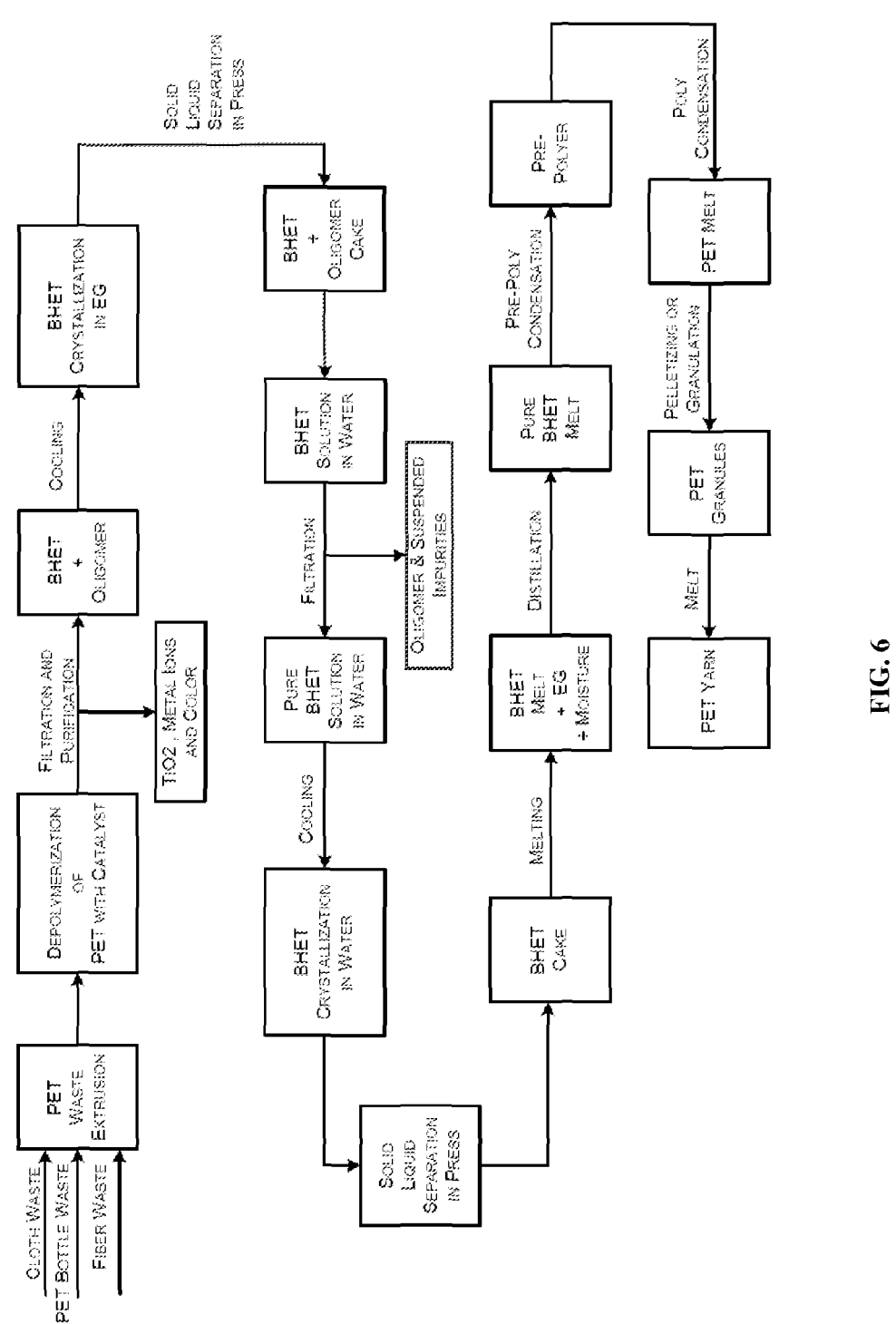
FIG. 6 illustrates an exemplary flow chart depicting a process for production of PET yam from PET waste in accordance with an embodiment of the present disclosure, as detailed hereinabove.

FIG. 6 illustrates an exemplary flow chart depicting a process for production of PET yarn from PET waste in accordance with an embodiment of the present disclosure, as detailed hereinabove.

Although several embodiments of the present disclosure are detailed/explained with reference to recycling or regeneration of polyethylene terephthalate (PET) waste, it should be appreciated that the advantageous process of the instant disclosure can also be implemented in or as part of the production units for polyethylene terephthalate (PET) products including PET bottles, polyester yarns and the likes. For example, the advantageous process of the present disclosure may be implemented as part of the polyester yarn production unit, wherein the polyester yarn wastes generated during the production process may be subjected to the process of the present disclosure to regenerate/produce PET polymers that can either be directly used for production of polyester yarns or can be mixed with virgin/fresh PET polymers in desired proportions to effect production of polyester yarns. Alternatively, the process of the instant disclosure may be implemented as a separate industrial unit that can take up polyethylene terephthalate (PET) products (such as refused products, wastes generated during production of PET products or consumer led plastic wastes such as municipal plastic wastes) and effect production of bis(2-hydroxyethyl) terephthalate (BHET) and/or PET polymer that may be sold as raw material.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

EXAMPLES

Pulverized PET wastes having mean particle size of 346 microns (50.6% particles having size between 270-500 microns) were taken. Table 1 below provides properties of the PET wastes used in the experiments.

TABLE 1

| | | | | | | | M.P. | |
| Properties of Different Types of PET based Wastes | | | | | | | | |
| | Luster | IV | COOH Gr | DEG % | Ash % | Color b | (° C.) Peak | Sb2O3 (ppm) |
| --- | --- | --- | --- | --- | --- | --- | --- | --- |
| PET Bottle flakes | Colorless | 0.730 | 39 | 1.58 | 0.029 | 2.6 | 247.6 | 274 |
| PET Bright Yarn Waste | Colorless | 0.621 | 41 | 1.41 | 0.133 | 1.3 | 258.2 | 220 |
| Bright PET Yarn waste POPCORN | Colorless | 0.546 | 58 | 1.49 | 0.160 | 1.10 | 259.4 | 224 |
| Semi dull PET Yarn Waste POPCORN | White | 0.506 | 60 | 1.58 | 0.273 | 5.10 | 259.3 | 214 |

100 grams of different pulverized PET wastes (shown in Table 1) were subjected to the process of the instant disclosure (as shown in FIG. 1). Reaction conditions during the partial polymerization and the depolymerization reaction as well as results obtained therefrom are provided in Table 2 below.

about 63.0% PET remaining therein (denoted as "% Oligomer") and intrinsic viscosity of the partially depolymerized mixture was about 0.047. The partially depolymerized PET mixture was 5 then mixed with additional ethylene glycol in a weight ratio of about 1:2.5 (PET:EG weight ratio, calculated based on the initial weight of PET), and 500 ppm

TABLE 2

|  |  |  | Partial depolymerization | | | | | Properties after depolymerization | |
| --- | --- | --- | --- | --- | --- | --- | --- | --- | --- |
| Exp. No- | PET waste | Partial Depolymerization conditions | Initial IV | Final IV | End gr. | % Oligomer | Depolymerization conditions | Sampling time | % Oligomer |
| 1 | PET Bright Yarn waste | PET:EG ratio = 1:0.5, 500 ppm zinc acetate, 40 min, Temp. 200-230 C. | 0.621 | 0.042 | 66 | 69.4 | PET:EG ratio = 1:1.5, 500 ppm Zinc Acetate at Temp. 190-195° C., 4 Hrs. (Total Ratio 1:2) | 2 Hrs. 3 Hrs. 4 Hrs. | 22.50 12.50 11.90 |
| 2 | PET Bright Yarn waste | PET:EG ratio = 1:0.5, 500 ppm zinc acetate, 40 min, Temp. 200-230 C. | 0.621 | 0.047 | 107 | 63.0 | PET:EG ratio = 1:2.5, 500 ppm Zinc Acetate at Temp. 190-195° C. 4 Hrs. (Total Ratio 1:3) | 2 Hrs. 3 Hrs. 4 Hrs. | 6.90 5.20 5.10 |
| 3 | PET Bottle flakes | PET: EG ratio = 1:0.5, 500 ppm zinc acetate, 40 min, Temp. 200-230° C. | 0.73 | 0.047 | 20 | 69.0 | PET:EG ratio = 1:3, 500 ppm Zinc Acetate at Temp. 190-195° C., 5 Hrs. (Total Ratio 1:3.5) | 2 Hrs. 3 Hrs. 4 Hrs. 5 Hrs. | 4.62 4.30 4.51 4.41 |

Title of Table 2: Depolymerization of PET in two-step process employing depolymerization catalyst in the partial depolymerization step As can be seen from Table 2 (Exp. No. 2), 100 gm of tolten PET Bright Yam waste was mixed with ethylene glycol at a weight ratio of 1:0.5 (PET:EG) 10 and 500 ppm of zinc acetate catalyst was added thereto maintaining a temperature in the range of 200-230'C for a period of about 40 minutes to effect partial depolymerization of the PET waste. As can also be seen from Table 2 (Exp. No. 2), initial intrinsic viscosity of the PET Bright Yam waste was about 0.621 as measured in 60:40 Phenol:Dichlorobenzene mixed solvent at 25 deg C. After partial depolymerization (at the end of 40 minutes), the partially depolymerized mixture had of zinc acetate was added thereto maintaining the temperature at 190° C. to 195° C. The reaction mixture was sampled at different time periods (after 2 hours, 3 hours and 4 hours) to monitor progress of the reaction. It could be observed that after 4 hours the PET waste was fully 10 depolymerized (only –5.1% of PET remained in the reaction mixture). Similar observation was made when PET Bottle flakes was subjected to the process (Exp. No. 3 in the Table 2 above).

TABLE 3

|  |  | Partial Depoly- | Partial Depolymerization | | | | | Properties after Depolymerization | |
| --- | --- | --- | --- | --- | --- | --- | --- | --- | --- |
| Trial No- | Type of PET waste | merization conditions | Initial IV | Final IV | End gr. | % Oligomer | Depolymerization conditions | Sampling time | % Oligomer |
| 1 | PET Bright POPCORN waste | PET: EG ratio = 1:0.5, 40 min, Temp. 200-210 C. | 0.554 | 0.051 | 41 | 73.4 | PET:EG ratio = 1:3.0, 500 PPM Zinc Acetate at Temp. 190-195° C. 4 Hrs. (Total Ratio 1:3.5 ) | After 2 Hrs. After 3 Hrs. After 4 Hrs. | 5.59 5.50 5.32 |
| 2 |  |  |  |  |  |  | PET:EG ratio = 1:2.25, 500 PPM Zinc Acetate at Temp. 190-195° C. 4 Hrs. (Total Ratio 1:2.75 ) | After 2 Hrs. After 3 Hrs. After 4 Hrs. | 10.56 9.96 9.89 |

Title of Table 3: Depolymerization of PET in two-step process without employing depolymerization catalyst in the partial depolymerization step

COMPARATIVE EXAMPLES

To understand the effect of the step of partial depolymerization on the overall depolymerization of the PET waste, several experiments were performed using different PET based wastes at different process conditions precluding the step of partial depolymerization, results whereof are provided in Table 4 below.

TABLE 4

Depolymerization of PET in single step process

| Exp. no. | Sampling time | wt. of PET waste (gm) | wt. of PET in initial mixture (gm) | wt. of oligomer/ PET remaining in mixture (gm) | % Oligomer/ PET remaining in mixture | Reaction conditions |
|---|---|---|---|---|---|---|
| 1 | 2 hrs | 100 | 33.33 | 6.6166 | 19.85 | Pulverized |
| | 3 hrs | 100 | 33.33 | 6.5394 | 19.62 | BRT Chips; |
| | 4 hrs | 100 | 33.33 | 5.8775 | 17.63 | PET:EG = 1:2; |
| | 5 hrs | 100 | 33.33 | 5.8021 | 17.41 | zinc acetate |
| | 6 hrs | 100 | 33.33 | 5.6021 | 16.81 | 1000 ppm, |
| | 7 hrs | 100 | 33.33 | 5.5510 | 16.65 | Temp. 190- |
| | | | | | | 195° C. |
| 2 | 3 hrs | 100 | 33.33 | 9.2582 | 27.78 | Pulverized |
| | 4 hrs | 100 | 33.33 | 7.3182 | 21.96 | BRT Chips; |
| | 5 hrs | 100 | 33.33 | 6.1892 | 18.57 | PET:EG = 1:2; |
| | 6 hrs | 100 | 33.33 | 5.9963 | 17.99 | Zinc Acetate |
| | 7 hrs | 100 | 33.33 | 5.8209 | 17.46 | 2000 ppm, |
| | 8 hrs | 100 | 33.33 | 5.5508 | 16.65 | Temp. 190- |
| | 9 hrs | 100 | 33.33 | 5.4668 | 16.40 | 195° C. |
| | 10 hrs | 100 | 33.33 | 5.2365 | 15.71 | |
| 3 | 3 hrs | 100 | 25.00 | 3.6617 | 14.65 | Pulverized |
| | 4 hrs | 100 | 25.00 | 3.5784 | 14.31 | BRT. Chips, |
| | 5 hrs | 100 | 25.00 | 3.4173 | 13.67 | PET:EG = 1:3, |
| | 6 hrs | 100 | 25.00 | 3.3900 | 13.56 | Catalyst 2000 |
| | 7 hrs | 100 | 25.00 | 3.3600 | 13.44 | ppm Zinc |
| | 8 hrs | 100 | 25.00 | 3.2564 | 13.03 | Acetate, Temp. |
| | 9 hrs | 100 | 25.00 | 3.2612 | 13.04 | 190-195° C. |
| | 10 hrs | 100 | 25.00 | 3.2428 | 12.97 | |
| | 11 hrs | 100 | 25.00 | 3.1600 | 12.64 | |
| | 12 hrs | 100 | 25.00 | 3.1390 | 12.56 | |
| | 13 hrs | 100 | 25.00 | 3.1289 | 12.52 | |
| 4 | 2 hrs | 100 | 20.00 | 1.8029 | 9.01 | Pulverized |
| | 3 hrs | 100 | 20.00 | 1.6891 | 8.45 | BRT Chips, |
| | 4 hrs | 100 | 20.00 | 1.3428 | 6.71 | PET:EG = 1:4, |
| | 5 hrs | 100 | 20.00 | 1.3548 | 6.77 | Catalyst 1000 |
| | 6 hrs | 100 | 20.00 | 1.1780 | 5.89 | ppm zinc |
| | | | | | | acetate, Temp. |
| | | | | | | 190-195° C. |
| 5 | 4 hrs | 100 | 20.00 | 1.7020 | 8.51 | PET bottle |
| | 5 hrs | 100 | 20.00 | 1.4563 | 7.28 | flakes, |
| | | | | | | PET:EG = 1:4, |
| | | | | | | Catalyst 1000 |
| | | | | | | ppm Zinc |
| | | | | | | acetate, Temp. |
| | | | | | | 190-195° C. |
| 6 | 4 hrs | 100 | 20.00 | 2.1563 | 10.78 | BRT. |
| | 5 hrs | 100 | 20.00 | 1.8563 | 9.28 | POPCORN, |
| | | | | | | PET:EG = 1:4, |
| | | | | | | catalyst 1000 |
| | | | | | | ppm Zinc |
| | | | | | | acetate, Temp. |
| | | | | | | 190-195° C. |

As can be seen from Table 4 (Exp. No. 5) above, when the step of partial depolymerization was precluded, even after 5 hours, 7.28% of oligomers remained in the mixture (i.e., PET oligomers that could not be depolymerized) when ethylene glycol was mixed in the PET:EG weight ratio 1:4 and 1000 ppm zinc acetate was used. In comparison, when the PET waste (PET bottle flakes) was subjected to the step of partial depolymerization before effecting depolymerization thereof (See, Table 2, Exp. No. 3), with use of PET:EG weight ratio of about 1:3.5 (1:0.5 during partial polymerization and additional EG at a ratio of 1:3 during depolymerization) and 1000 ppm zinc acetate, the reaction was complete after about 3 hours (i.e., only about 4.3% PET polymer remained after 3 hours).

Further, as can be seen from Table 4 (Exp. No. 6) above, when the step of partial depolymerization was precluded, even after 5 hours, 9.28% of PET oligomers remained in the mixture (i.e., PET oligomers that could not be depolymerized) when ethylene glycol was mixed in the PET:EG weight ratio 1:4 and 1000 ppm zinc acetate was used. In comparison, when the PET waste (PET bottle flakes) was subjected to the step of partial depolymerization before effecting depolymerization thereof (See. Table 3. Exp. No. 1), with use of PET:EG weight ratio of about 1:3.5 (1:0.5 during partial polymerization and additional EG at a ratio of 1:3 during depolymerization) and addition of 500 ppm zinc acetate (without addition of zinc acetate during the step of partial depolymerization), the reaction was complete after about 4 hours (i.e., only about 5.32% PET oligomer remained after 4 hours).

Accordingly, it is clear that the advantageous process of the instant disclosure affords depolymerization of PET waste at a significantly reduced amounts of ethylene glycol (i.e., saving of at least 500 kg of ethylene glycol for each ton of PET waste) and/or at a significantly reduced amounts of depolymerization catalyst coupled with reduced reaction time (i.e., 3-4 hours reaction time as compared to 5-6 hours when the step of partial depolymerization is not done) and improved yield.

Production of Recycled Pet from Pet Bottle Flakes

For partial depolymerization, 8 kgs of bottle flakes having intrinsic viscosity (IV) of 0.73 dl/gm as measured in 60:40 Phenol:Dichlorobenzene mixed solvent at 25 deg C. were partially depolymerized with 4 kgs of Mono Ethylene Glycol (EG) and 4 grams of Zinc acetate in a reaction vessel having reflux system at 220 deg C. for 1 hr. IV of depolymerized product was 0.046 dl/gm and was having about 77% oligomer. IV of the separated oligomer was 0.052 and melting point was 151.9 deg C. This indicates the extent of depolymerization. For glycolysis (depolymerization), 12 kgs of the partial depolymerized product was fed to a reaction vessel. This vessel was already having 24 kgs of EG at 150 deg C. under atmospheric pressure with stirring, 4 grams of catalyst Zinc acetate was added to EG during feeding to the vessel. The temperature of reaction vessel was raised to 195 deg C. in 30 minutes and depolymerization reaction was continued for 3 hours at 195 deg C. Every hour sampling was done to check the extent of glycolysis. It could be observed that within 3 hours, level of oligomer % in glycolysis product was below 5%. The crude product mixture was then passed through a mesh filter (80 mesh) and cooled down to about 90° C. The cooled down product mixture was passed through a series of filters maintained at 85° C. to 90° C. for reduction of color and metal ion impurities present therein. The first filter was activated charcoal filter (Auro Carbon & Chemical. India) having bulk density 0.53 gm/cc, and iodine adsorption 700 mg/gm; the second filter was cation exchange resin (Purolite Pvt. Ltd.) having carboxyl functional group; the third filter was anion exchange resin (Purolite Pvt. Ltd.) having proprietary chromium selective functional group; and the fourth filter was of diatomaceous earth material type (Amol Minechem Ltd, Ahmedabad) having bulk density 0.245 gm/cc and mean particle size of 8.0 microns. The residence time for the filtration was 20 minutes. The depolymerized (glycolyzed)

product after filtration was 35.7 kg and loss was due to removal of moisture along with small fraction of EG.

After filtration, about 18 kg of recycled Ethylene Glycol (EG) was mixed with the glycolyzed product. The mixture was cooled down to about 22° C., so that BHET is separated out through crystallization. The mixture having crystallized BHET was then put into a filter press to separate out excess EG from BHET. The EG content in the cake was about 37%. The separated EG from the press filter was recycled for depolymerization and crystallization.

About 8 kg of the cake was taken in a vessel and 32 kg hot water (having temp of about 95° C.) was added thereto with stirring to prepare an immersion mixture. After 60

Shimadzu Corp. after sample digestion, Ash % was measured by ignition and charring the sample in a silica crucible kept into a muffle furnace at 800 deg C. for 2 hrs. and by weight difference. Melting temperature (° C.) was measured by taking sample in a aluminum pan and by differential scanning calorimeter of Perkin Elmer. Color values L, a & b (the color space) (referred to herein as "L-color", "a-color" and "b-color") represent the color space defined by the Hunter Lab, which expresses color as three values—"L" for perceptual lightness, "a" for red to green and "b" for blue to yellow, which was measured by Spectrophotomerter (X-rite Inc).

TABLE 5

Properties of crude product mixture and filtered BHET

| | Crude Product Mixture | | | | | Filtered BHET | | | | |
|---|---|---|---|---|---|---|---|---|---|---|
| Product | IV (dl/gm) | COOH End Group | DEG % | Ash % | Color b | IV | COOH End Group | DEG % | Ash % | Color b |
| Bottle Flakes | 0.033 | 6 | 1.14 | 0.012 | 1.27 | 0.027 | 5 | 1.07 | 0.006 | 1.51 |
| Semi Bright yarn waste Popcorn + Flake (50/50%) | 0.027 | 8 | 1.21 | 0.011 | 0.51 | 0.020 | 6 | 1.16 | 0.005 | 0.69 | minutes, the immersion mixture was filtered through 3 micron nonwoven filter. The filtered immersion mixture was cooled down to about 22° C. and 10 kg recycled water was added thereto for crystallization of BHET. The mixture with the crystallized BHET was put into a filter press to separate out excess water and to obtain the purified BHET. The cake (purified BHET) so obtained had about 35% water and about 10% ethylene glycol.

For polymerization, 14 kg molten purified BHET (140° C.) was charged into a reaction vessel having an agitator with torque measurement & condenser with vacuum facility, 2.4 gm Antimony Trioxide catalyst (Huachang, China) was also added along with molten BHET. Initial temperature after material charge was kept at 210° C. and vacuum was applied at 800 mbar to remove moisture and EG. Gradually temperature was increased to 270° C. and vacuum was also made finer to 20 mbar over a period of 2 hours. Under the temperature and vacuum, BHET started polymerizing with removal of EG, and IV of the polymer was about 0.260. Thereafter, the partially polymerized material was transferred to other reaction vessel and vacuum of 2 mbar and temperature of 275° C. was maintained for a period of 1 hour with continuous agitation and torque measurement. Reaction was monitored with regular torque measurement. Quantity of the recycled PET obtained was about 7.4 kg.

Table 5 below provides properties of the resultant crude product mixture and of the filtered BHET, Table 6 below provides properties of the resultant dried purified BHET, and Table 7 below provides properties of the recycled PET, wherein Intrinsic Viscosity (referred to herein as "IV" with unit dl/gm) was measured in Phenol/Dichlorobenzene 60:40 mixture at 25 deg C. in Ubbelohde viscometer. Carboxyl end group (referred to herein as "End Gr." with unit meq./kg) was measured in Phenol/chloroform 50/50 mixture after refluxing and cooling to room temp by titration with 0.05 N Benzyl alcoholic KOH, Diethylene Glycol % (referred to herein as "DEG %") was measured by gas chromatograph of

TABLE 6

Properties of dried purified BHET

| Product | IV | Carboxyl End Gr | DEG % | Ash % | Melting Temp. ° C. | Color L | Color a | Color b |
|---|---|---|---|---|---|---|---|---|
| Bottle Flakes | 0.05 | 11 | 0.54 | 0.01 | 111.2 | 87.80 | 0.16 | 3.01 |
| Semi Bright yarn waste Popcorn + Flakes (50/50%) | 0.048 | 10 | 0.58 | 0.009 | 111.6 | 87.58 | 0.25 | 2.76 |

TABLE 7

Properties of recycled PET

| IV | End Gr | DEG % | Ash % | L-color | a-color | b-color | Melting temp. (° C.) |
|---|---|---|---|---|---|---|---|
| 0.671 | 33 | 1.45 | 0.043 | 41.6 | 1.0 | 7.10 | 254.2 |

Production of BHET from Bottle Flakes and Semi Bright Yarn Popcorn (50/50%)

BHET was prepared from mixed 50150% bottle flakes and semi bright yarn POPCORN, wherein 4 kg of bottle flakes (IV –0.730) and 4 kg of semi 10 bright yam waste POPCORN (IV –0.546) were fed to the reaction vessel. The same process, as exemplified in the above example (i.e., "production of recycled PET from bottle flakes") was followed for production of BHET. Properties of the resultant crude product mixture and of purified BHET are provided in Table 5 above and Properties of the resultant dried purified BHET is provided in Table 6 above.

Depolymerization of Pet in Two-Step Process at Pilot Scale (without Employing Depolymerization Catalyst in the Partial Depolymerization Step)

Partial depolymerization of PET melt from extruder in presence of EG without catalyst with ratio of 1:0.5 (PET: EG) was performed. Extruder melt temperature was 260 C and flow rate was 10 kgs per hr. EG was mixed with molten polymer at the flow rate of 5 kgs per hr. The residence time of mixture was 30 minutes before feeding to the glycolysis (depolymerization) vessel. The glycolysis vessel was having 70 kgs of EG at 195 C with 500 ppm of zinc acetate based on PET. Partially depolymerized product was fed to the glycolysis vessel for 2 hrs. After completion of feeding to glycolysis vessel, sampling was started after 1 hr, 2 hrs and 3 hrs. Oligomer % was checked for each sample to find out extent of glycolysis. Bright chips IV was 0.632. After extruder melting with EG. IV of feed material to glycolysis vessel was in the range of 0.08-0.11. This drop in IV indicated significant amount of depolymerization. In glycolysis (complete depolymerisation step), there was a reduction (improvement) in oligomer %. After 2-3 hrs, oligomer % reached to around 3%. This pilot scale experiment confirmed scalability of the process of the present disclosure with retention of the advantages mentioned herein. Reaction conditions during the partial polymerization and the depolymerization reaction as well as results obtained therefrom are provided in Table 8 below.

TABLE 8

| | | | | | | Glycolysis condition of | Properties after glycolysis | |
|---|---|---|---|---|---|---|---|---|
| | | Partial | After melt Product Properties | | | | | |
| Trial No- | PET waste | depolymerization condition | Chips IV | End IV | % gr. | Oligomer | molten product | Sampling time | % Oligomer |

Advantages

The present disclosure provides a process for production of bis(2-hydroxyethyl) terephthalate (BHET) from polyethylene terephthalate (PET) that is relatively simple, safe, environment friendly and cost-effective.

The present disclosure provides a process for production of BHET from PET that affords depolymerization of PET at a significantly reduced amounts of ethylene glycol.

The present disclosure provides a process for production of bis(2-hydroxyethyl) terephthalate (BHET) from polyethylene terephthalate (PET) that affords depolymerization of PET within short time period as compared to conventional processes.

The present disclosure provides a process for production of BHET from PET that affords depolymerization of PET at a significantly reduced amounts of depolymerization catalyst.

The present disclosure provides a process for recycling of polyethylene terephthalate (PET) that affords higher yields.

The present disclosure provides a process for recycling of polyethylene terephthalate (PET) from polyethylene terephthalate (PET) waste.

The present disclosure provides a process for recycling of polyethylene terephthalate (PET) from polyethylene terephthalate (PET) waste that is significantly economical, relatively simple, environment friendly and capable of implementation at an industrial scale.

We claim:
1. A process for production of bis(2-hydroxyethyl) terephthalate (BHET) from polyethylene terephthalate (PET), said process comprising the steps of:
partially depolymerizing of the polyethylene terephthalate (PET) by mixing the polyethylene terephthalate (PET) with ethylene glycol in a weight ratio of PET:ethylene glycol ranging from 1:0.3 to 1:1.5 while maintaining temperature of the mixture in a range of 200° C. to 250° C. to obtain a partially depolymerized polyethylene terephthalate (PET), wherein the partial depolymerization is effected in absence of a depolymerization catalyst; and
depolymerizing the partially depolymerized polyethylene terephthalate (PET) by contacting the partially depolymerized polyethylene terephthalate (PET) with ethylene glycol in a weight ratio of PET:ethylene glycol ranging from 1:1 to 1:4 in presence of the depolymerization catalyst at a temperature ranging from 170° C. to 200° C. for a time period ranging from 2 hours to 5 hours, to produce crude product mixture comprising bis(2-hydroxyethyl) terephthalate (BHET).
2. The process as claimed in claim 1, wherein said polyethylene terephthalate (PET) comprises polyethylene terephthalate (PET) waste selected from the group consisting of at least one of: PET bottle flakes, PET yarn, PET thermoformed packages, PET fabric, bright PET yarn waste popcorn, semi dull PET yarn waste popcorn.
3. The process as claimed in claim 1, wherein said polyethylene terephthalate (PET) comprises polyethylene terephthalate (PET) waste having an intrinsic viscosity ranging from 0.5 to 0.8 as measured in 60:40 Phenol:Dichlorobenzene mixed solvent at 25° C., a melting point ranging from 240° C. to 260° C., and an ash content ranging from 0.03% to 2.0% by weight.
4. The process as claimed in claim 1, wherein the step of partial depolymerization of polyethylene terephthalate (PET) comprises:
exposing polyethylene terephthalate (PET) to a temperature ranging from 240° C. to 330° C. to obtain molten polyethylene terephthalate (PET); and
contacting the molten polyethylene terephthalate (PET) with hot ethylene glycol in a weight ratio of PET: ethylene glycol ranging from 1:0.3 to 1:1.5 while maintaining the temperature of the mixture in a range of 200° C. to 250° C. to obtain partially depolymerized polyethylene terephthalate (PET).
5. The process as claimed in claim 4, wherein the hot ethylene glycol has a temperature ranging from 180° C. to 190° C.
6. A process for recycling of polyethylene terephthalate (PET) from polyethylene terephthalate (PET) waste, said process comprising the steps of:
partially depolymerizing the polyethylene terephthalate (PET) waste by mixing the polyethylene terephthalate (PET) waste with ethylene glycol in a weight ratio of

PET:ethylene glycol ranging from 1:0.3 to 1:1.5 while maintaining a temperature of the mixture in a range of 200° C. to 250° C. to obtain a partially depolymerized polyethylene terephthalate (PET);

depolymerizing the partially depolymerized polyethylene terephthalate (PET) by contacting the partially depolymerized polyethylene terephthalate (PET) with ethylene glycol in a weight ratio of PET:ethylene glycol ranging from 1:1 to 1:4 in the presence of a depolymerization catalyst at a temperature ranging from 170° C. to 200° C. for a time period ranging from 2 hours to 5 hours to produce a crude product mixture comprising bis(2-hydroxyethyl) terephthalate (BHET);

purifying the crude product mixture to obtain purified bis(2-hydroxy ethyl) terephthalate BHET); and polymerizing the purified bis(2-hydroxyethyl) terephthalate (BHET) in the presence of a polymerization catalyst at a temperature ranging from 200° C. to 300° C. and at a pressure ranging from 50 mbar to 2 mbar for a time period ranging from 2 hours to 5 hours to obtain the recycled polyethylene terephthalate (PET).

7. The process as claimed in claim 6, wherein the polyethylene terephthalate (PET) waste is selected from the group consisting of one or more of: PET bottle flakes, PET yarn, PET thermoformed packages, PET fabric, bright PET yarn waste popcorn, semi dull PET yarn waste popcorn, having an intrinsic viscosity ranging from 0.5 to 0.8 as measured in 60:40 Phenol:Dichlorobenzene mixed solvent at 25° C., a melting point ranging from 240° C. to 260° C., and an ash content ranging from 0.03% to 2.0%.

8. The process as claimed in claim 6, wherein the step of partial depolymerization of the polyethylene terephthalate (PET) waste comprises:

exposing the polyethylene terephthalate (PET) waste to a temperature ranging from 240° C. to 330° C. to obtain molten polyethylene terephthalate (PET); and contacting the molten polyethylene terephthalate (PET) with hot ethylene glycol in a weight ratio of PET:ethylene glycol ranging from 1:0.3 to 1:1.5, to obtain partially depolymerized polyethylene terephthalate (PET).

9. The process as claimed in claim 6, wherein the depolymerization catalyst is a metal based catalyst, the metal being selected from the group consisting of at least one of zinc, titanium and antimony, and wherein the polymerization catalyst is selected from the group consisting of Antimony Trioxide, Antimony Triacetate, Antimony Glycolate, and Germanium Dioxide.

10. The process as claimed in claim 6, wherein depolymerizing the partially depolymerized polyethylene terephthalate (PET) step comprises contacting the partially depolymerized polyethylene terephthalate (PET) with the ethylene glycol in the presence of the depolymerization catalyst comprising zinc acetate in an amount ranging from 400 ppm to 1400 ppm.

11. The process as claimed in claim 6, wherein the step of purification of the crude product mixture comprises:

filtering the crude product mixture;

crystallizing bis(2-hydroxyethyl) terephthalate (BHET) from the filtered crude product mixture;

separating crystallized bis(2-hydroxyethyl) terephthalate (BHET) to obtain a cake comprising bis(2-hydroxyethyl) terephthalate (BHET);

immersing the cake in a hot water in a weight ratio ranging from 1:4 to 1:8 to obtain an immersion mixture, said hot water having temperature ranging from 90° C. to 98° C.;

recrystallizing the bis(2-hydroxyethyl) terephthalate (BHET) from the immersion mixture; and separating the recrystallized bis(2-hydroxyethyl) terephthalate (BHET) to obtain purified bis(2-hydroxyethyl) terephthalate (BHET).

12. A method for production of bis(2-hydroxyethyl) terephthalate (BHET) from polyethylene terephthalate (PET), comprising:

feeding polyethylene terephthalate (PET) and ethylene glycol into a first reaction vessel, wherein polyethylene terephthalate (PET) and the ethylene glycol are in a weight ratio of PET:ethylene glycol ranging from 1:0.3 to 1:1.5;

maintaining the first reaction vessel at a temperature in a range of 200° C. to 250°, resulting in partially depolymerized polyethylene terephthalate (PET);

feeding the partially depolymerized polyethylene terephthalate (PET) and ethylene glycol into a second reaction vessel having a depolymerization catalyst, wherein the partially depolymerized polyethylene terephthalate (PET) and the ethylene glycol are in a weight ratio of PET:ethylene glycol ranging from 1:1 to 1:4; and maintaining the second reaction vessel at a temperature ranging from 170° C. to 200° C. for a time period ranging from 2 hours to 5 hours, resulting in a crude product mixture comprising bis(2-hydroxyethyl) terephthalate (BHET), wherein the first reaction vessel may be the same or different from the second reaction vessel; and wherein the depolymerization catalyst is not present in the first reaction vessel when the polyethylene terephthalate (PET) and ethylene glycol are fed into the first reaction vessel.

13. The system method as claimed in claim 12, wherein said polyethylene terephthalate (PET) comprises polyethylene terephthalate (PET) waste selected from the group consisting of at least one of: PET bottle flakes, PET yarn, PET thermoformed packages, PET fabric, bright PET yarn waste popcorn, semi dull PET yarn waste popcorn.

14. The method as claimed in claim 12, wherein said polyethylene terephthalate (PET) comprises polyethylene terephthalate (PET) waste having an intrinsic viscosity ranging from 0.5 to 0.8 as measured in 60:40 Phenol:Dichlorobenzene mixed solvent at 25° C., a melting point ranging from 240° C. to 260° C., and an ash content ranging from 0.03% to 2.0% by weight.

15. The method as claimed in claim 12, further comprising heating the polyethylene terephthalate (PET) in the first vessel to a temperature ranging from 240° C. to 330° C. to obtain molten polyethylene terephthalate (PET), and receiving hot ethylene glycol in the first vessel and mixing the received hot ethylene glycol with the molten polyethylene terephthalate (PET) in a weight ratio of PET:ethylene glycol ranging from 1:0.3 to 1:1.5, while maintaining the mixture at a temperature in a range of 200° C. to 250° C., to obtain the partially depolymerized polyethylene terephthalate (PET).

16. The method as claimed in claim 15, wherein the hot ethylene glycol is received into the first vessel at a temperature ranging from 180° C. to 190° C.

17. The method as claimed in claim 12, wherein the depolymerization catalyst comprises zinc acetate present in the second vessel in an amount ranging from 400 ppm to 1400 ppm.

18. The process as claimed in claim 1, further comprising:

purifying the crude product mixture to obtain purified bis(2-hydroxy ethyl) terephthalate (BHET); and polymerizing the purified bis(2-hydroxyethyl) terephthalate (BHET) in the presence of a polymerization catalyst at a temperature ranging from 200° C. to 300° C. and at a pressure ranging from 50 mbar to 2 mbar for a time period ranging from 2 hours to 5 hours to obtain the recycled polyethylene terephthalate (PET).

19. The process as claimed in claim 18, wherein the step of purifying comprises:

filtering the crude product mixture;

crystallizing bis(2-hydroxyethyl) terephthalate (BHET) from the filtered crude product mixture;

separating crystallized bis(2-hydroxyethyl) terephthalate (BHET) to obtain a cake comprising bis(2-hydroxyethyl) terephthalate (BHET);

immersing the cake in a hot water in a weight ratio ranging from 1:4 to 1:8 to obtain an immersion mixture, said hot water having temperature ranging from 90° C. to 98° C.;

recrystallizing the bis(2-hydroxyethyl) terephthalate (BHET) from the immersion mixture; and separating the recrystallized bis(2-hydroxyethyl) terephthalate (BHET) to obtain purified bis(2-hydroxyethyl) terephthalate (BHET).

20. The process as claimed in claim 6, wherein the depolymerizing is conducted at a temperature ranging from 180° C. to 190° C.

* * * * *